US00PP34355P2

(12) United States Plant Patent
Ledesma

(10) Patent No.: US PP34,355 P2
(45) Date of Patent: Jun. 21, 2022

(54) MANGO TREE NAMED 'CHERRY'

(50) Latin Name: *Mangifera indica*
Varietal Denomination: Cherry

(71) Applicant: Noris Ledesma, Miami, FL (US)

(72) Inventor: Noris Ledesma, Miami, FL (US)

( * ) Notice: Subject to any disclaimer, the term of this patent is extended or adjusted under 35 U.S.C. 154(b) by 0 days.

(21) Appl. No.: 17/510,435

(22) Filed: Oct. 26, 2021

(51) Int. Cl.
*A01H 5/08* (2018.01)

(52) U.S. Cl.
USPC ..... Plt./159

(58) Field of Classification Search
USPC ..... Plt./159
See application file for complete search history.

*Primary Examiner* — Annette H Para

(57) ABSTRACT

New variety of mango tree (*Mangifera indica*), 'Cherry', is disclosed; distinguished by production of heavy and consistent crops with fruit weighting 1,030 g (36.3 oz) on average, having rounded base with a shallow cavity, small beak and smooth surface except for few small lenticels. Skin is thick and resistant to anthracnose. Mature fruit has brilliant oxblood red peel color confluent over nearly the whole surface. Immature fruits are purple with an ashen, waxy sheen. When ripe, the fruit has a pleasant apricot aroma with accents of peach, papaya, and a hint of coconut; flesh is tangerine orange, firm and melting without fiber. It has a floral bouquet with a hint of sugar cane, a creamy smooth texture with 17.5°±1 brix and long flavor-life in storage. The tree is small with round spreading canopy, highly productive and good disease tolerance. The new 'Cherry' tree has potential for commercial use.

4 Drawing Sheets

Genus and species: *Mangifera indica.*
Variety denomination: 'Cherry'.

BACKGROUND OF THE NEW PLANT

The present invention comprises a new and distinct variety of mango tree, botanically known as *Mangifera indica*, and hereinafter referred to by the variety name 'Cherry'.

'Cherry' is a new variety of mango tree discovered as a seedling that was derived from open pollination of what was discovered as an improved seedling selection of mango tree named 'Kent' (unpatented) and was selected for remarkable qualities when compared with 'Kent'. Selection of the new variety was made on Jun. 1, 2018, at a private mango farm in the Redlands farming district of Miami-Dade County in south Florida, the United States of America and was made based on improved characteristics including disease resistance, brighter color, its small tree size, and good fruit quality. Asexual propagation of the new variety by grafting using cuttings was first performed in July 2018 using mature mango trees as a topworking graft rootstock 6 years old. The propagation was done at a private mango farm in the Redlands farming district of Miami-Dade County in south Florida, the United States of America.

The new 'Cherry' variety is distinguished by the production of heavy and consistent crops of fruit which are 1,030 g (36.3 oz) average weight, with a rounded base with a shallow cavity; small beak and smooth surface except for few and small lenticels. The mature fruit has a brilliant oxblood red peel color confluent over nearly the whole surface. Immature fruits are purple with an ashen, waxy skin. Ripe fruit has a pleasant apricot aroma with accents of peach, papaya, and a hint of coconut. The flesh is tangerine orange, firm and melting without fiber. It has pleasant flavor of apricot with accents of peach, papaya, and a hint of coconut. The flesh is tangerine orange, firm and melting without fiber, creamy and with smooth texture with a brix of 17.5°±1 and a long flavor-life in storage. The skin is thick and resistant to anthracnose disease. The tree is small, forming a round canopy. Trees in South Florida reach a height of 1.6-3.0 m (5.2-9.8 ft), a spread of 2.2 m (7 ft)—but with annual pruning they can be kept smaller. The tree flushes once a year with short internodes. It is a small tree size and highly productive, with excellent disease tolerance. It has a polyembryonic seed with a weight average of 131 gr (4.6 oz), and are 9.6 cm (3.8 in) long, 5.08 cm (2.0 in) wide and 3.55 cm (1.4 in) thick.

The new 'Cherry' tree has been asexually propagated via grafting using cuttings and has been found to retain its distinctive characteristics through asexual propagations.

Plant Breeder's Rights for this variety have not been applied for. The new variety 'Cherry' has not been made publicly available or sold anywhere in the world more than one year prior to the effective filing date of this application.

SUMMARY OF THE INVENTION

The following are the most outstanding and distinguishing characteristics of this new cultivar when grown at the Redlands farming district of Miami-Dade County in south Florida, the United States of America and can be used to distinguish 'Cherry' as a new and distinct variety of mango tree:

1. Excellent quality of fruit with brighter and uniform oxblood red peel color.
2. Small tree size with heavy and consistent crops.
3. Excellent disease tolerance.

DESCRIPTION OF THE PHOTOGRAPHS

This new mango tree is illustrated by the accompanying photographs which show the entire tree, the inside and outside of the fruit, and the seed; the colors shown are as true as can be reasonably obtained by conventional photographic procedures. The photographs are of a 3-year-old tree using topworking graft rootstock 6 years old tree grown at a private mango farm in the Redlands farming district of Miami-Dade County in south Florida, the United States of America. Pictures of flowers and inflorescence were taken in January 2020 and pictures of tree and fruit were taken in July 2021.

FIG. 1 shows the entire tree.

FIG. 2 shows the exterior and interior of the mature fruit and the seed.

FIG. 3 shows the inflorescence and flowers.

FIG. 4 shows the leaves.

DESCRIPTION OF THE NEW VARIETY

The following detailed descriptions set forth the distinctive characteristics of 'Cherry'. Trees of the new mango variety have not been observed under all possible environmental conditions. Observations and measurements were taken on a 3-year-old tree using topworking graft rootstock of a 6 year old tree, grown at a private mango farm in the Redlands farming district of Miami-Dade County in south Florida, the United States of America.

Color readings were taken under natural light. Color references are primarily to The R.H.S. Colour Chart of The Royal Horticultural Society of London (R.H.S.) (2016 edition).

DETAILED BOTANICAL DESCRIPTION

Classification:

*Family*.—Anacardiaceae.

*Botanical name*.—*Mangifera indica*.

*Denomination*.—'Cherry'.

Tree:

*Growth habit*.—Spreading and rounded.

*Height*.—1.6 m (5.2 ft) high.

*Regularity of bearing*.—Regular bearing.

*Productivity*.—Very good; 15.6 kg (34.4 pound) per tree.

*Pollinator information*.—Main pollinators are flies.

Trunk:

*Diameter*.—12.0 cm (4.7 in) at 0.8 m (2.6 ft) height.

*Surface texture*.—Smooth and regular.

*Color*.—Gray-brown, consistent with trunk color of other mango varieties (approximately RHS 199A).

Branches:

*Habit*.—Spreading and open.

*Surface texture*.—Smooth and regular Color (one year old and older): Same as trunk.

*Size*.—91.4 cm (36 in) average.

*Growth flows*.—Once a year between 5.8 cm to 9.9 cm (2.3 in to 3.9 in).

Leaves:

*General size*.—Smaller compared with other mango varieties.

*Length*.—14.0 cm (5.5 in).

*Width*.—3.0 cm (1.18 in).

*Shape*.—Lanceolate.

*Apex*.—Acute.

*Base*.—Broad angular.

*Margin*.—Smooth to slightly wavy.

*Shape in cross-section*.—Incurved.

*Pubescence*.—Absent.

*Color*.—Upper surface: Green (RHS 139A). Lower surface: Typically, the same as upper (green), or with a slightly more yellow green (RHS 146B). Color (immature): Greyed-orange (RHS 177B).

*Petiole*.—Length: 1.1 cm to 1.9 cm (0.43 in to 0.74 in). Diameter: 0.3 cm to 0.4 cm (0.12 in to 0.16 in). Color (mature): Yellow-green (RHS 146B). Color (immature): Greyed-red (RHS 178B).

Inflorescence:

*General*.—Flowers produced on terminal inflorescences with thousands of individual flowers that typically set less than 1.5% in natural pollination. Inflorescence is pyramidal, 36.5 cm (14.4 in) long, with dense flowering.

*Date of bloom*.—Mid-December to early March.

Flower bud:

*Length*.—2.5 mm (0.10 in).

*Surface texture*.—Surface is firm.

Flowers: Flowers have high percentage of hermaphrodite flowers (52% to 72%) compared with other cultivars. Petals and sepals: Both male and hermaphrodite flowers have 5 petals and sepals. Flower buds are both male and hermaphrodite: Size: 2.5 mm (0.10 in) and average surface texture and, when fully open: 4.1 mm (0.16 in). Petals: Quantity per flower: 5, Color: White to cream gray (RHS 155A) to brown red (RHS 178B) with maturity Sepals: Quantity per flower: 5; Peduncle: Small and many-branched, Color: Pink to brown red (RHS 178B) or green (RHS 138B).

Reproductive organs:

*Anther quantity*.—5 per flower.

*Anther color*.—White (RHS 155A).

*Ovary quantity*.—1.

*Stigma color*.—White (RHS 155A) and red closer to the center of the flower (/RHS 178B).

Fruit: General: The fruit are ripe for commercial harvesting and shipment approximately June through July in the Redlands farming district of Miami-Dade County in south Florida, the United States of America. The fruit are large, Length: Typical average length: 14.8 cm (5.8 in); Diameter: Typical average diameter: 12.5 cm (4.9 in); Thickness: Typical average thickness: 11.2 cm (4.4 in); Weight: Typical average weight: 1,030 g (36.3 oz). Shape: Oblong to oval with an undulating skin surface, a rounded base with a shallow cavity, slender stem with a squared insertion, and a small lateral beak; Surface: Slightly wavy; Appendix: Lightly dotted; Peak: Small; side Shape of peak: Bluntly pointed Stem. Peduncle: Hard, cylindrical; Length: 10.0 cm (3.94 in) to 16.0 cm (6.30 in); Diameter: 0.3 cm (0.12 in); Color: Brown to gray (RHS 199C); Skin: Thickness: Thick, leathery and adhesive; Smoothness: Moderately undulating; Lenticels: Few, small, yellow lenticels (RHS 162B); Color: Immature fruit turn purpure (RHS 59A), and when they ripe fruit turned brilliant oxblood red peel color (RHS 60B) confluent over nearly the whole surface. Flesh: Texture: Firm, melting, and juicy without fiber; Color: Tangerine-orange (RHS 24A). Flavor: Excellent flavor reminiscent of apricot with accents of peach, papaya, and a hint of coconut. It has creamy smooth texture with a brix of 17.5°±1 and a long flavor-life in storage. Fragrance: Slight and pleasant. Seed: General: Polyembryonic; Shape: Oblong-oval, Length: 9.6 cm (3.8 in); Breadth: 5.08 cm (2.0 in); Thickness: 3.55 cm (1.4 in), Weight: 131.0 g (4.6 oz). Texture: Thick and woody; tied to the pulp Softening:

Time to softening (ripening) depends on stage of maturity (3 to 10 days); softening is uniform and rapid once it begins yet flesh firmness is maintained for several days at room temperature. Use: Mango pulp and juice, Keeping quality: Above average shipping and shelf life, Harvesting: By hand.

Disease resistance: Anthracnose (*Colletotricum gloeosporioides*): Good tolerance; Powdery mildew (*Oidium mangiferae*): Moderate susceptibility.

Physiological conditions: Sap burn is not a problem.

The new 'Cherry' variety differs from the parent tree 'Kent' (unpatented) in that 'Cherry' produces fruit that are uniform in shape where most fruit are oblong to oval with a rounded base and shallow cavity with an average weight of 1,030 g (36.3 oz). The new mango 'Cherry' immature fruits are purple with an ashen, waxy skin, and when ripen turned brilliant oxblood red peel color confluent over nearly the whole surface, and the tree is small, and spreading and rounded and highly productive, with good disease tolerance. 'Kent' produces fruit average 600 g (21.2 oz) that varies in shape where some are more elongated and some are rounded, and the base color is green with yellow and some red blush. Additionally, the tree is vigorous, large, and compact canopy and susceptible to Anthracnose (*Colletotricum gloeosporioides*) when grown under the same environmental conditions in the Redlands farming district of Miami-Dade County in south Florida, the United States of America.

'Cherry' differs from commercial mango variety 'Haden' (unpatented) in that 'Cherry' produces large fruit with an oblong to oval shape, whereas 'Haden' produces medium to large fruit with an oval to round shape.

I claim:

1. The invention of a new and distinct cultivar of mango tree named 'Cherry', characterized by a small size tree with heavy and consistent crops, excellent quality of fruit with brighter and uniform oxblood red color and excellent disease tolerance, substantially as illustrated and described in the specification.

* * * * *

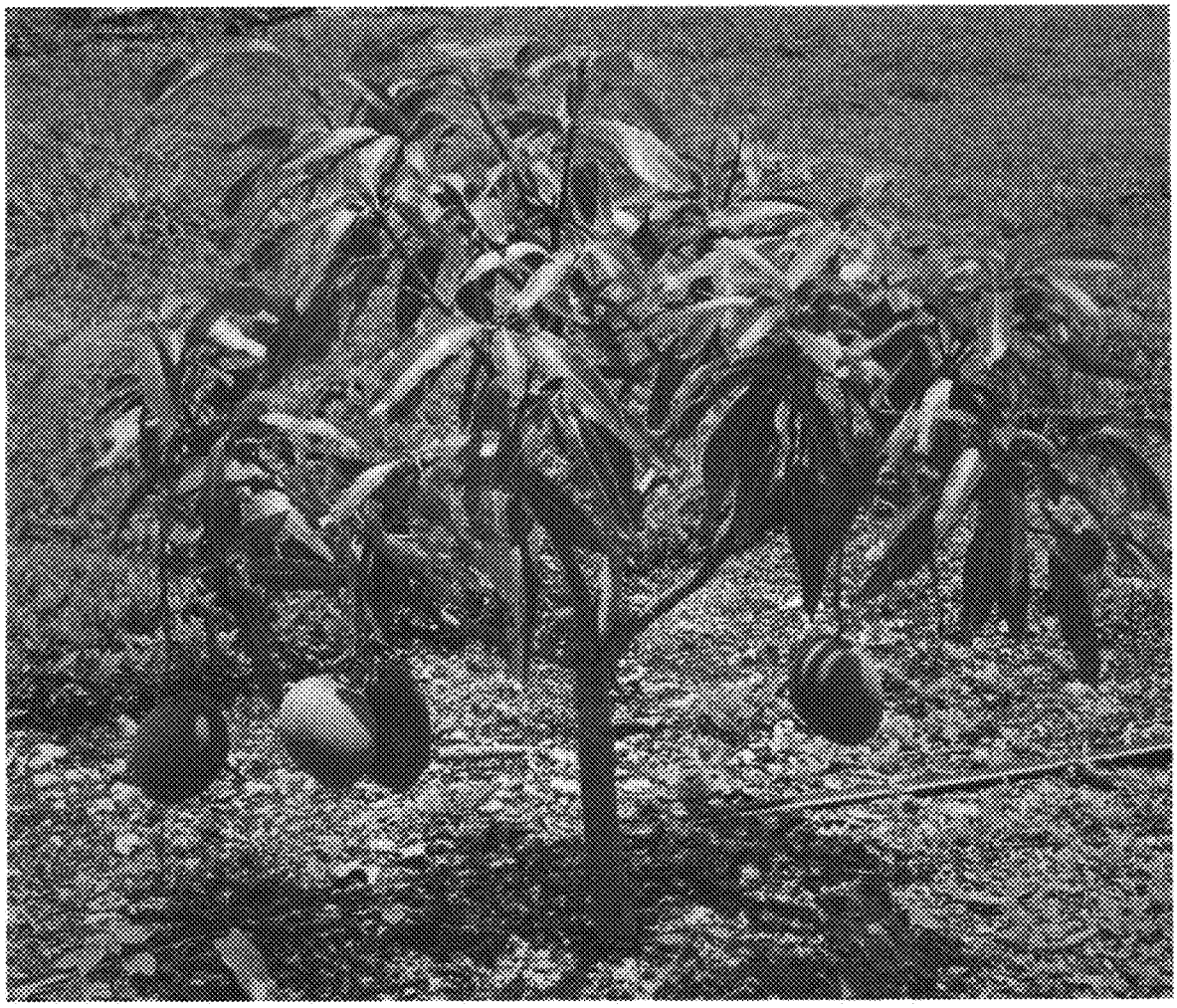
FIG. 1 shows the entire tree

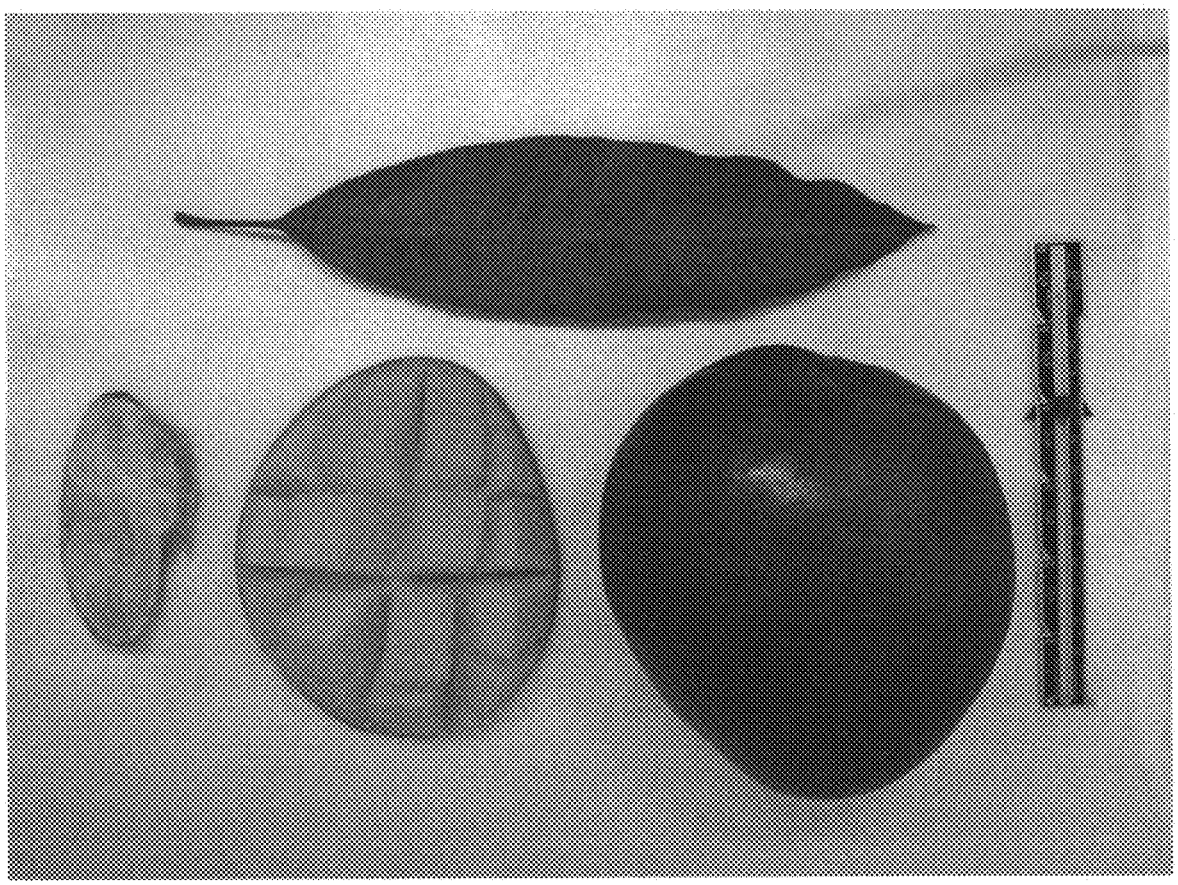
FIG. 2 shows the exterior and interior of the mature fruit and the seed

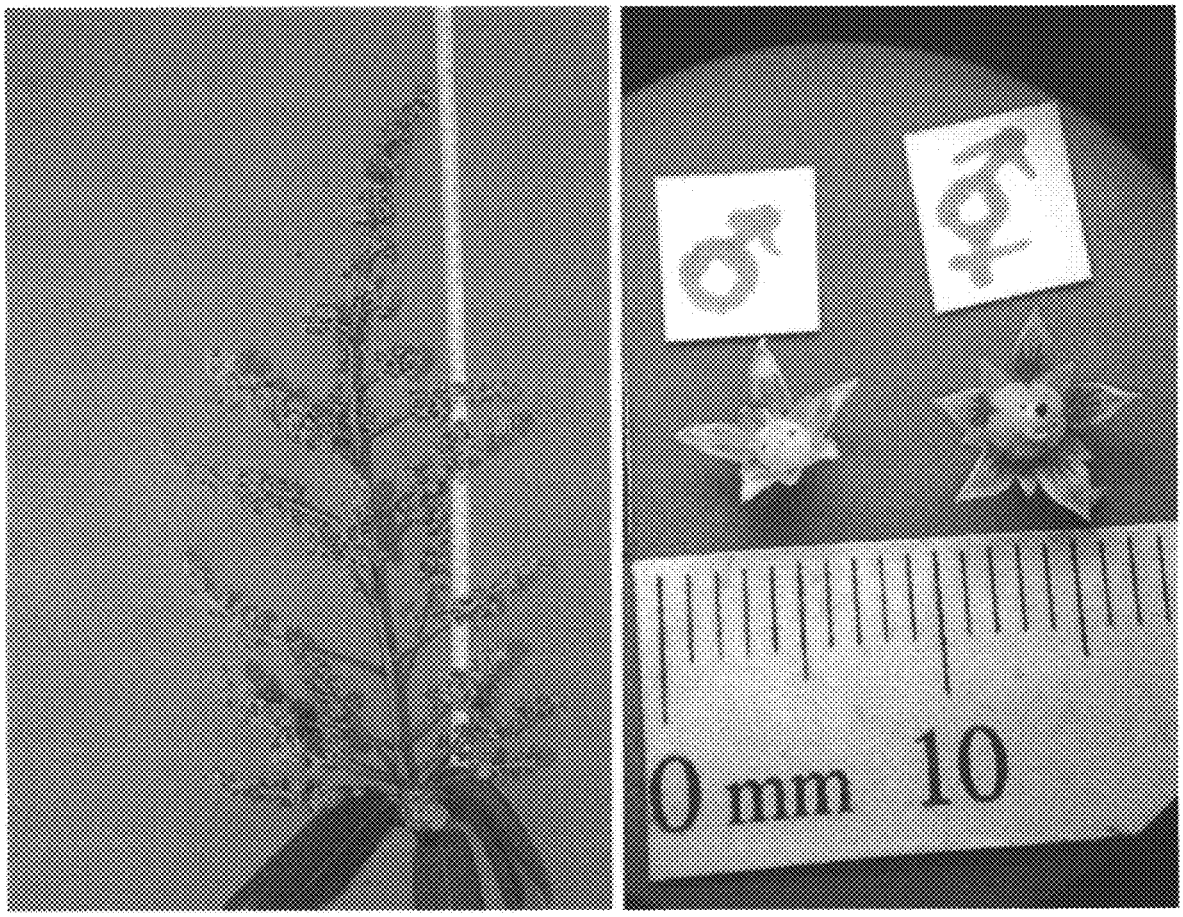
FIG. 3 shows the inflorescence and flowers

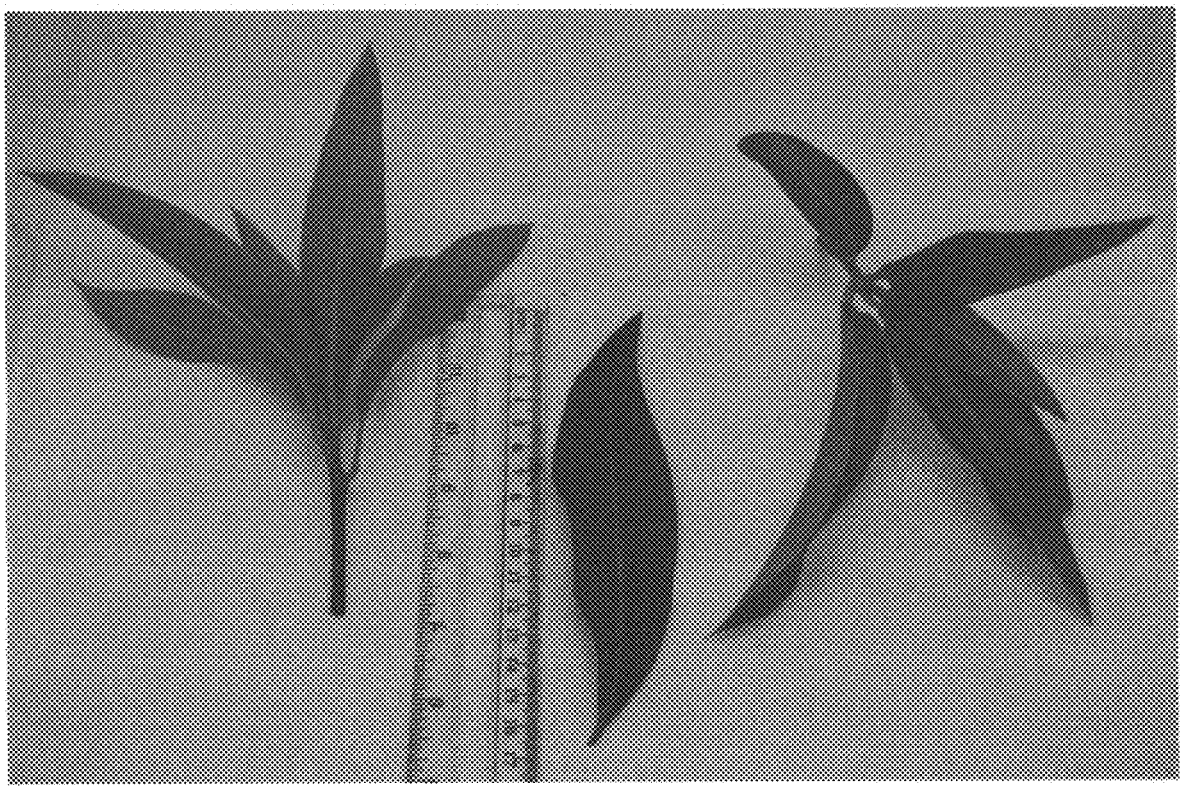
FIG. 4 shows the leaves